United States Patent [19]

Bopp

[11] Patent Number: 4,468,461

[45] Date of Patent: Aug. 28, 1984

[54] MICROBIOLOGICAL REMOVAL OF CHROMATE FROM CONTAMINATED WASTE WATER

[75] Inventor: Lawrence H. Bopp, Scotia, N.Y.

[73] Assignee: General Electric Company, Schenectady, N.Y.

[21] Appl. No.: 329,494

[22] Filed: Dec. 10, 1981

[51] Int. Cl.$^3$ .................... C12N 1/20; C12P 3/00; C12R 1/39
[52] U.S. Cl. .................... 435/253; 435/262; 435/168; 435/876; 210/611; 210/913
[58] Field of Search ............... 435/253, 168, 876, 800, 435/262; 210/611, 913

[56] References Cited

U.S. PATENT DOCUMENTS

| | | | |
|---|---|---|---|
| 3,736,239 | 5/1973 | George et al. | 210/913 |
| 3,941,691 | 3/1976 | Romanenko et al. | 210/2 |
| 4,127,447 | 11/1978 | Griffith et al. | 435/813 |
| 4,159,944 | 7/1979 | Erickson et al. | 210/611 |
| 4,321,149 | 3/1982 | Hawxhurst et al. | 210/913 |

OTHER PUBLICATIONS

Yakovlev et al., "Biochemical Treatment of Industrial Waste Water Containing Hexavalent Chromium Compounds" Vodosnabzh. Sanit. Tekh. (1974) (5) pp. 7–10 Chemical Abstracts 81:96047s.

Karyukhima et al., "Biological Treatment of Waste Water in the Presence of Chemically Bound Oxygen" Vodosnabzh. Sanit. Tekh. 1979 (3) pp. 9–11 Chemical Abstracts 94:35642m.

Summers et al. "Metal Cation and Oxyanion Resistances in Plasmids of Gram–Negative Bacteria" Microbiology (1978) pp. 128–131 Chemical Abstracts 88:117637.

Hawley, "The Condensed Chemical Dictionary" Eighth Edition (1971) Van Nostrand Reinhold Company p. 212.

Bopp, "Chromate Resistance and Chromate Reduction in Bacteria" Dissertation Abstracts Int. B. (1981) 41 (8) p. 2900–2901.

V. I. Romanenko, et al., "A Pure Culture of Bacteria Utilizing Chromates and Bichromates as Hydrogen Acceptors in Growth Under Anaerobic Conditions", [Mikrobiologiya 46, pp. 414–417 (1977)].

*Primary Examiner*—Alvin E. Taneholtz
*Assistant Examiner*—John Edward Tarcza
*Attorney, Agent, or Firm*—Leo I. MaLossi; James C. Davis, Jr.; James Magee, Jr.

[57] ABSTRACT

A new strain of *Pseudomonas fluorescens* is disclosed for use in the removal of chromate from waste water.

9 Claims, No Drawings

MICROBIOLOGICAL REMOVAL OF CHROMATE FROM CONTAMINATED WASTE WATER

BACKGROUND OF THE INVENTION

Certain industrial processes such as electroplating generate waste waters containing high concentration of chromate. Also, waste solutions from the production of sodium chromate from chromite ore contain high chromate concentrations. Chromate is very toxic, and there is convincing evidence that it is both mutagenic and carcinogenic. It is, therefore, important that chromate be removed from contaminated water before that water is returned to the environment.

Chromate can be removed from solution by the use of a chemical reducing agent. Such agents reduce the chromium from $Cr^{+6}$ to $Cr^{+3}$, in which form it can be precipitated. Other methods of chromate removal involve dialysis of chromate-bearing wastes and the use of ion-exchange methods. These latter approaches do not require chromate reduction.

Disclosure of the capability of *Pseudomonas dechromaticans* to biochemically reduce chromates and bichromates only under anaerobic conditions is found in U.S. Pat. No. 3,941,691—Romanenko et al. This same work has also been reported in the literature, "A Pure Culture of Bacteria Utilizing Chromates and Bichromates As Hydrogen Acceptors in Growth Under Anaerobic Conditions" by Romanenko and Korenkov [Mikrobiologiya 46, pp. 414–17 (1977)]. In addition, it has been reported by Lebedeva and Lyalikova in "Reduction of Crocoite by *Pseudomonas chromatophila* sp. nov." [Mikrobiologiya 48, pp. 517–22 (1979)] that the chromium in the mineral crocoite ($PbCrO_4$) can be reduced only under anaerobic conditions to $Cr^{+3}$ by *Pseudomonas chromatophila*.

Chromate is very toxic to normal microorganisms, most of which cannot tolerate concentrations of $K_2CrO_4$ higher than 10–20 ppm in minimal salts media. Included among the microorganisms sensitive to chromate are those microorganisms necessary for the digestion of sewage. Therefore, the introduction of waste water containing elevated chromate levels into sewage digesters poses an additional problem over and above the health problems engendered by the release of chromate to the environment.

DESCRIPTION OF THE INVENTION

The instant invention is directed to a process employing a specific strain of bacterium (LB300) isolated from the Hudson River in Upstate New York, which strain most closely fits the taxonomic classification of *Pseudomonas fluorescens*, for the reduction of chromate from $Cr^{+6}$ to $Cr^{+3}$ in which form the chromium will precipitate from waste water contaminated therewith. Unlike other strains of *P. fluorescens*, LB300 possesses both chromate resistance and the ability to reduce chromate.

In one form of this invention, waste water contaminated with chromate is passed through a series of holding ponds containing the special bacteria of this invention before returning the treated waste water to the environment. The number of ponds in series is dependent upon the specific requirements for cleanup of the expected or known chromate contamination.

Another manner in which the invention may be practiced is in connection with domestic sewage treatment systems. The specific bacterium of this invention can be used to detoxify chromate in a contaminated sewage digester in which the microflora have been killed by chromate-bearing sewage input. After detoxification the normal microflora can be reestablished.

The microorganism strain of this invention is effective in reducing chromate under aerobic or, optionally, under anaerobic conditions. In the application of this invention first noted above, the nutritional requirements of the organisms can be satisfied by continually adding small amounts of domestic sewage to the first pond in series. This strain is capable of utilizing an unusually diverse variety of organic substrates for growth.

MANNER AND PROCESS OF MAKING AND USING THE INVENTION

For the practice of this invention, a culture of this microorganism designated LB300 is on deposit with the U.S. Department of Agriculture as *P. fluorescens* (NRRL B-12596).

In the event that during pendency of this application the Commissioner of Patents and Trademarks shall determine that some individual is entitled to receive progeny of this strain under the conditions imposed by 37 CFR 1.14 and 35 U.S.C. 122, the requisite written authorization will be provided by the assignee of this application.

Upon the issuance of this application as a patent, a sub-culture of this strain can be obtained from the permanent collection of the Agricultural Research Culture Collection (NRRL) at the Northern Regional Research Center, U.S. Department of Agriculture, Peoria, Ill., U.S.A.

Physiological characteristics of this strain indicating its particular adaptability to the above-noted applications are as follows:

1. Growth and chromate reduction occur at temperatures from below 4° C. to approximately 35° C. This means that this organism can reduce chromate under any conditions of temperature likely to be encountered in a holding pond or sewage digester.

2. Several growth substrates have been found to be satisfactory for both growth and chromate reduction. Among those tested are glucose, acetate, pyruvate, lactate, and succinate. In addition, it is known that *Pseudomonas fluorescens* strains are capable of utilizing an unusually diverse variety of organic substrates for growth. This is important because it means that almost anything organic can be used to fulfill the nutritional requirements of this bacterium.

3. This organism is a facultative anaerobe capable of growth in the absence of $O_2$, using the normal biochemical pathways and substituting nitrate or nitrite for $O_2$ as the terminal electron acceptor. In addition, this organism has the capability of growing anaerobically using chromate as the terminal electron acceptor. This capability allows the organism to grow and reduce chromate even in the anaerobic sediment of the holding ponds. Also, in unstirred ponds that do not freeze to the bottom in winter, anaerobic zones develop. Thus, the development of anaerobic zones would not prevent chromate reduction from occurring.

4. This strain is resistant to concentrations of $K_2CrO_4$ as high as 2000 ppm in a minimal salts medium, while other bacteria tested could not grow in the same medium when the concentration exceeded 10–20 ppm. It is unlikely that any industrial effluent would contain chromate at such a concentration that it would be toxic to this strain.

5. The reduction of chromate is an enzymatic process, which will occur in actively growing cells or in resting cells that are provided with an organic reductant, such as glucose. This means that it is not necessary to optimize growth conditions in order to have chromate reduction, as long as the cells are supplied with an organic reductant.

6. The growth rate is not affected by concentrations of $K_2CrO_4$ up to 250 ppm. This fact means that having to adjust for different growth rates in different holding ponds in a series is not necessary as long as the concentration does not exceed 250 ppm (as $K_2CrO_4$).

7. Under laboratory conditions either actively growing or resting cells can reduce the concentration of chromate from 250 ppm to less than 10 ppm in a period of 24 hours.

8. The $Cr^{+6}$ is reduced to $Cr^{+3}$, the only other stable oxidation state for chromium, by this bacterium. The $Cr^{+3}$ forms insoluble hydroxides and precipitates, thus effectively removing the chromium from solution. $Cr^{+3}$ is much less toxic to bacteria than $Cr^{+6}$ and so its accumulation in the holding pond sediments is not a problem. This process of chromate removal can be enhanced by the addition of negatively charged particles to the waste water, such as clays, which should help immobilize the chromium precipitate in the sediments.

9. This bacterium can be stored in a dormant state in 50% glycerine at $-20°$ C. for more than a year and then be revitalized in a few hours. The doubling time under ideal conditions is about 30 minutes. It is therefore a simple matter to produce a large, active inoculum when the need arises.

The LB300 bacterium of this invention is non-pathogenic and has been observed to exhibit some resistance to bichromate. Whether or not LB300 has the ability to reduce bichromate has not, however, been determined with certainty. LB300 is a variant of *P. fluorescens* in that all the characteristics of LB300 set forth in Table I below, except its behavior in gelatin hydrolysis, reflect the same behavior as is characteristic of *P. fluorescens*.

TABLE I

| TEST | LB300 |
|---|---|
| ONPG hydrolysis | − |
| alcohol dehydrogenase | + |
| lysine decarboxylase | − |
| ornithine decarboxylase | − |
| citrulline | − |
| H$_2$S production | − |
| urease | − |
| tryptophan deaminase | − |
| indole | − |
| gelatin hydrolysis | − |
| glucose fermentation | − |
| glucose oxidation | + |
| NO$_3$→NO$_2$ | + |
| motility | + |
| growth on MacConkey agar | + |
| cetrimide resistance | + |
| gram stain | − |
| cytochrome oxidase | + |
| growth at 4° C. | + |
| growth at 41° C. | − |

Chromate resistance, but not the ability to reduce chromate, was found to be plasmid-associated. The plasmid could be transferred to sensitive strains of *P. fluorescens* and *Escherichia coli*. Chromate resistance appears to be the result of lowered membrane permeability to chromate. Chromate reduction has been shown to be a form of anaerobic respiration in this *P. fluorescens* strain. The enzyme system is constitutive. The product of chromate reduction is mainly in the form of chromium hydroxide precipitates.

In the preferred method for the microbiological removal of chromate from contaminated waste water, which has a significant particle content, this result may be accomplished by employing a series of holding ponds constructed such that the untreated waste water containing chromate enters the first in the series and the outflow therefrom enters the second in the series and so on with the outflow of the last in the series returning the water to the environment via a river, sewage system, or some other channel. The entire system is innoculated with active cultures of LB300, the *P. fluorescens* strain of this invention.

The number of ponds employed in series is dependent upon the specific requirements of the chromate removal task. Once the system has been established, the rate of input will be the same as the rate of outflow from the series of ponds. The turnover time in a given pond can be adjusted by adjusting the size of the pond. For example, if the chromate concentration in the first pond in the series were so high that it restricted the growth of the microorganisms, it would be necessary for this pond to be larger than the next pond in the series. Otherwise the organisms would be removed via the out-flow faster than they could multiply and the population in the initial pond in the series would be reduced to extinction.

The metabolic activity of these organisms can be increased by aeration and agitation. Thus, if it is desirable to accelerate the rate of chromate reduction in any given pond in the series or in all ponds in the series, aeration and agitation would be utilized.

The nutritional requirements of these organisms can be satisfied by the continuous addition of small amounts of domestic sewage to the first pond in the series. Some of this sewage will spill over into the next pond in the series, but will be digested by the time the effluent is ready for return to normal disposal channels. The overflow of microorganisms from one pond to the next in the series will assure satisfactory nutrient supply even in the last pond in the series.

Removal of the microorganisms from the final outflow is not necessary, since they are normal soil and water bacteria and do not cause environmental problems. However, it is possible to remove cell mass and undigested constituents of the sewage input simply be directing the outflow from the last pond into evaporation basins. The organic residue can then be recovered and used as fertilizer or used to supplement the nutrient supply in the first pond in the series.

The above-noted process can be used to remove chromate from any aqueous solution that contains less than 2000 ppm $K_2CrO_4$ (or equivalent) and that does not contain any other constituents that prevent growth of the microorganisms of this invention.

In the second application of the microorganisms of this invention, a digester for domestic sewage, which has become contaminated with chromate such that the indigenous, or normal, microflora are no longer viable, can be inoculated with actively growing cultures of the organisms of this invention and chromate content of the digester can be reduced to the less toxic form ($Cr^{+3}$) which will not inhibit the growth of normal microorganisms even at high concentrations. As a result, the microbial reduction of chromate eliminates the toxicity problem in the digester and normal microflora can be reestablished by the addition of an inoculum of uncontaminated digest from another source.

In the case of an aerobic sewage digester, aeration and stirring are normally provided and these factors will assist in the rapid reduction of the chromate present, since the metabolic activity of the microorganisms is increased. In the case of anaerobic digesters, the organism can be made to grow rapidly simply by pumping air into the digester using a compressor and sparger.

The level of chromate in a digester can be monitored spectrophotometrically at 388 nm. Samples must be cleared of particulate matter before absorbance readings can be taken. This can be accomplished by low speed centrifugation followed by filtering through 0.45 micron filters. By following absorbance at 388 nm as described and comparing it to a standard curve, it is easy to tell when the chromate concentration has been sufficiently lowered.

This chromate-reducing bacterium can also be used in a prophylactic manner by establishing it in sewage digesters under normal operating conditions. Moderate influxes of chromate could then be handled without interrupting sewage processing. It might be necessary to maintain a small chemostat specifically for the growth of the chromate-reducing organisms such that the outflow from the chemostat is constantly supplying the digester(s) with fresh inoculum(a).

In those instances in which the contaminated flow is substantially particle-free, it is preferable to pass the flow through a packed column in which the LB300 microorganisms are immobilized on (e.g., adhere to) the packing material, which preferably comprises plastic beads or alginic acid beads. This procedure is particularly effective, since the enzyme responsible for reduction of chromate is located in the LB300 cell membrane and it is merely necessary to bring the flow into contact with the cell membrane. Other suitable packing materials and methods of preparation thereof are disclosed in U.S. Pat. No. 4,127,447 (column 2, lines 28-57). U.S. Pat. No. 4,127,447 is incorporated by reference. This approach has distinct advantages in that the overall size of the treatment plant can be greatly reduced and concomitantly a very large concentration (e.g., about $10^{12}$ cells per c.c. of column volume) of LB300 cells can be presented for contact with the flow being treated. Further, treatment in this way enables closer control on the process. Thus, pH control is particularly important in that the pH level should be high enough to optimize the enzyme activity, but low enough to reduce the precipitation of the chromium hydroxides in the column. As noted hereinabove, an organic reductant (e.g. glucose) has to be provided for the chromate reduction to proceed. Because it is merely necessary for the cells to be present in the column, it is expected that super-lethal concentrations of chromate can be treated. Still further, this arrangement facilitates periodic rinsing of the packed column with an acid solution to remove chromium hydroxides stuck to the beads and refurbish the activity of the column.

Performance illustrative of the capability for chromate reduction afforded by the packed column is shown by a typical run in which the chromate contamination in an aqueous solution was reduced in a period of 30 hours from 250 ppm $K_2CrO_4$ to about 2.5 ppm $K_2CrO_4$.

What I claim as new and desire to secure by Letters Patent of the United States is:

1. A biologically pure culture of a strain of *Pseudomonas fluorescens* having the identifying characteristics of *Pseudomonas fluorescens* NRRL B-12596, said characteristics including resistance to greater than 1000 ppm of chromate in minimal salts medium and the capability for reducing $Cr^{+6}$ to $Cr^{+3}$ in an aqueous medium in the presence of an organic reductant both under aerobic conditions and under anaerobic conditions, the $Cr^{+3}$ being in the form of a precipitate substantially insoluble in water at neutral pH.

2. The process of removing chromate from an aqueous medium contaminated with chromate comprising the steps of:
   a. contacting an aqueous medium with a culture of a strain of *Pseudomonas fluorescens* having the identifying characteristics of *Pseudomonas fluorescens* NRRL B-12596, said characteristics including being resistant to greater than 1000 ppm of chromate in minimal salts medium and having the capability for reducing $Cr^{+6}$ to $Cr^{+3}$ in aqueous media in the presence of an organic reductant both under aerobic conditions and under anaerobic conditions, the $Cr^{+3}$ being in the form of a precipitate substantially insoluble in water at neutral pH, and
   b. adding to said aqueous medium an amount of organic reductant effective to satisfy the nutritional requirements of the cells of said strain therein.

3. The process of claim 2 wherein the aqueous medium is domestic sewage having a chromate concentration significantly greater than the chromate level that is toxic to the indigenous microflora and the desired level of concentration of chromate is less than the toxic level.

4. The process of claim 2 wherein the aqueous medium is the waste water discharged from an industrial process.

5. The process of claim 2 wherein the aqueous medium is subjected to sufficient aeration to increase the rate of chromate reduction.

6. The process of claim 5 wherein the aqueous medium is simultaneously aerated and agitated.

7. The process of claim 2 wherein cells of the strain selected are immobilized on solid substrates.

8. The process of claim 7 wherein the pH level is controlled to optimize chromate reduction.

9. The process of claim 7 wherein the immobilized cells are periodically rinsed with an acid solution having a sufficiently low level of pH to cause chromium hydroxides to be dislodged from the solid substrates.

* * * * *